United States Patent [19]
Sullivan et al.

[11] Patent Number: 5,980,251
[45] Date of Patent: Nov. 9, 1999

[54] LAMINATED MAGNETOSTRICTIVE TRANSDUCER

[75] Inventors: John Sullivan, Wappinger Falls; Steven Abdelqader, Thiells, both of N.Y.

[73] Assignee: Coltene/Whaledent, Inc., Mahwah, N.J.

[21] Appl. No.: 08/906,575

[22] Filed: Aug. 5, 1997

[51] Int. Cl.$^6$ .............................. A61C 1/07; H02N 10/00
[52] U.S. Cl. .............................. 433/119; 318/118; 310/26
[58] Field of Search ............................ 433/119; 318/118; 310/26; 601/2; 604/22; 606/169

[56] References Cited

U.S. PATENT DOCUMENTS

| | | | |
|---|---|---|---|
| Re. 30,536 | 3/1981 | Perdreaux, Jr. ................... | 433/119 |
| 2,414,699 | 1/1947 | Olson et al. ...................... | 310/26 |
| 2,553,251 | 5/1951 | Gutterman ....................... | 310/26 |
| 2,636,998 | 4/1953 | Davis, Jr. et al. ................. | 310/26 |
| 2,842,067 | 7/1958 | Stevens . | |
| 2,890,354 | 6/1959 | McCown et al. ................. | 310/26 |
| 3,076,904 | 2/1963 | Kleesattel et al. ................ | 318/118 |
| 3,100,853 | 8/1963 | Kleesattel et al. . | |
| 3,102,210 | 8/1963 | Dory et al. ....................... | 310/26 |
| 3,471,724 | 10/1969 | Balamuth . | |
| 3,488,851 | 1/1970 | Haydu . | |
| 3,654,502 | 4/1972 | Carmona et al. ................. | 433/119 |
| 3,930,173 | 12/1975 | Banko ............................... | 310/26 |
| 4,281,987 | 8/1981 | Kleesattel ......................... | 433/119 |
| 4,492,574 | 1/1985 | Warrin et al. .................... | 433/81 |
| 4,505,676 | 3/1985 | Gonser ............................. | 433/119 |
| 4,820,152 | 4/1989 | Warrin et al. .................... | 433/119 |
| 4,986,808 | 1/1991 | Broadwin et al. ................ | 604/22 |
| 5,382,162 | 1/1995 | Sharp ................................ | 433/116 |
| 5,395,240 | 3/1995 | Paschke et al. .................. | 433/119 |
| 5,531,597 | 7/1996 | Foulkes et al. ................... | 433/119 |

*Primary Examiner*—Ralph A. Lewis
*Attorney, Agent, or Firm*—Helfgott & Karas, P. C.

[57] ABSTRACT

A magnetostrictive transducer including a plurality of magnetostrictive laminates each having a first end and a second end. The first and second ends of the laminates include openings. The laminates are arranged in a stacked configuration and bonded together by solder at the first and second ends. At the first and second ends the solder extends through the openings of the laminates forming a solder bar therein. The solder bars bond the laminates together with increased mechanical strength and also provide increased electrical contact between the laminates.

16 Claims, 3 Drawing Sheets

LAMINATED MAGNETOSTRICTIVE TRANSDUCER

BACKGROUND OF THE INVENTION

1. Field of the Invention

The present invention relates in general to ultrasonic medical or dental tools and, in particular, to an improved magnetostrictive transducer for ultrasonic medical or dental tools including an improved laminated structure that incorporates openings to bond the individual laminates.

2. Description of Prior Developments

Magnetostrictive transducers are well known devices for converting electrical energy into vibrational energy at ultrasonic frequencies. These devices are utilized in a variety of ultrasonic medical and dental tool applications including various types of dental scraping and scaling tools as well as surgical tools for fragmenting tissue.

One Example of such an application is disclosed in U.S. Pat. No. 5,382,162 to Sharp. As shown in FIG. 1, Sharp discloses an ultrasonic dental scaler which typically includes a dental scaler insert 2, a housing 10 and dental scaler electronics 16. The scaler insert 2 includes a magnetostrictive transducer 4, an O-ring 6 and a dental tool 8, as shown.

During operation, the scaler insert 2 is placed within the housing 10, wherein the O-ring 6 provides a water tight seal therebetween. Further, the magnetostrictive transducer 4 interacts with a magnetic field created by an energized coil 12 positioned on the housing 10 to vibrate the scaler insert 2. The scaler electronics 16 control the current supplied to the coil 12 so that the scaler insert 2 is vibrated at an ultrasonic frequency. This causes the dental tool 8 to be vibrated which enables it to scale teeth.

Conventional Magnetostrictive transducers of a laminated structure are described in such patents as U.S. Pat. No. 3,076,904 to Kleesattel, U.S. Pat. No. 3,930,173 to Banko and U.S. Pat. No. 4,986,808 to Broadwin et al. As shown in FIG. 2, such a laminated structure 18 typically includes a plurality of laminates 20 which are bonded together in a stacked configuration. The individual laminates 20 are elongated substantially flat members fabricated from magnetostrictive material such as nickel or a nickel alloy which are coated with a layer of oxide. The oxide serves to insulate the adjacent laminates from each other.

As is further evident from FIG. 2, the laminates 20 are bonded together at each end 22,24 by a brazing process. This brazing process produces brazed ends 22,24 having solder that covers all four sides of the stacked laminates 20. These brazed ends 22,24 are intended to keep the laminates 20 bonded together during operation as well as provide electrical contact between the laminates 20.

However, during operation, a problem arises in regard to these brazed ends 22,24. Since the magnetostrictive transducer 18 operates at an ultrasonic frequency, the individual laminates vibrate at this ultrasonic frequency. This vibration after a long period of time can cause metal fatigue in the abraded ends 22,24 which ultimately results in the solder cracking and the individual laminates 20 spreading part. Once the laminates 20 spread apart, the magnetostrictive transducer 18 is no longer functional and must be either replaced or repaired.

Further, conventional magnetostrictive transducers can also be difficult to fabricate. Since a large number of individual laminates are required to be bonded together, a significant amount of time is required to braze each of the ends. Also, the individual laminates are prone to be deformed during fabrication since the individual laminates are usually pushed along an assembly line before being bonded together.

In view of the above, a need therefor exists for a magnetostrictive transducer which is less susceptible to the metal fatigue that causes the laminations to spread apart. A further need exists for a magnetostrictive transducer that is more readily and easily fabricated.

SUMMARY OF THE INVENTION

The present invention has been developed to fulfill the needs noted above and therefore has as an object for the provision of a magnetostrictive transducer which is less susceptible to metal fatigue.

Another object of the invention is to provide a magnetostrictive transducer that provides greater electrical contact between the individual laminate ends.

Another object of the invention is to provide a magnetostrictive transducer that can be brazed in a shorter period of time.

Still another object of the invention is to provide a magnetostrictive transducer which can be fabricated without deformities in the individual laminates occurring.

These and other objects are met in accordance with the present invention which includes a plurality of magnetostrictive laminates each having a first end and a second end. The first and second ends of the laminates include openings. The laminates are arranged in a stacked configuration and bonded together by solder at the first and second ends. At the first and second ends the solder extends through the openings of the laminates forming a solder bar therein. The solder bars bond the laminates together with increased mechanical strength and also provide increased electrical contact between the laminate ends.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings.

In the various figures of the drawings, like reference characters designate like parts.

DETAILED DESCRIPTION OF THE PREFERRED EMBODIMENTS

Figure 1:
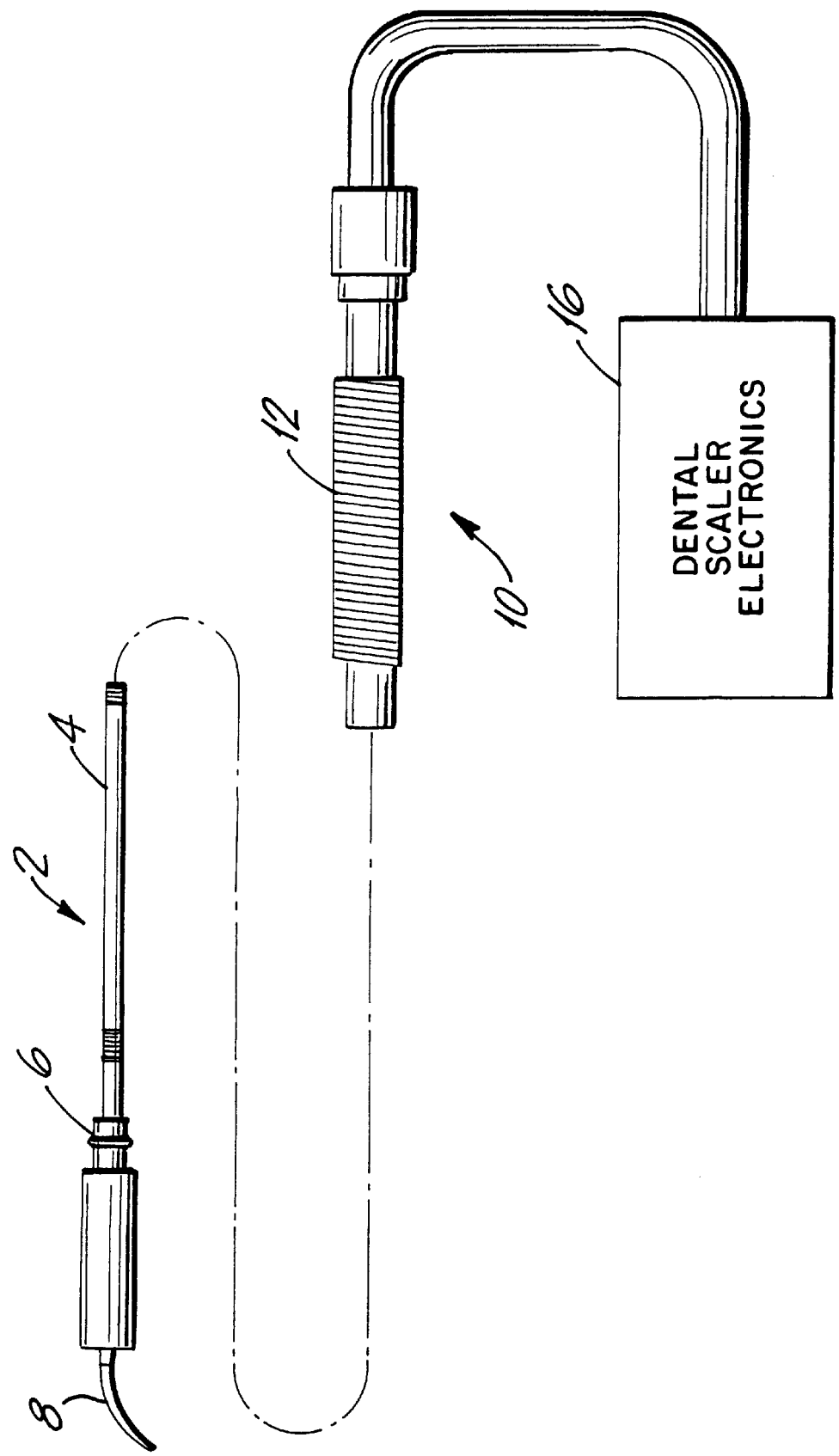
FIG. 1 is a diagram of a prior art ultrasonic dental scaler.
Figure 2:
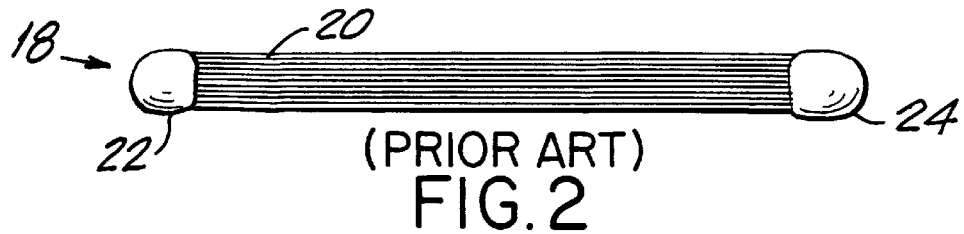
FIG. 2 is a top view of a prior art magnetostrictive transducer.
Figure 3:
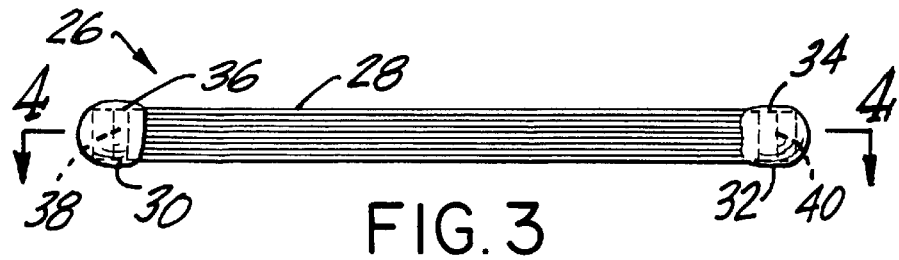
FIG. 3 is a top view of a magnetostrictive transducer according to the present invention.

The present invention will now be described in conjunction with the drawings beginning with FIG. 3 which depicts a magnetostrictive transducer 26 constructed according to the present invention.

The magnetostrictive transducer 26 according the present invention has a laminated structure similar to conventional devices, as described previously in the background of the invention, including a plurality of laminates 28 bonded together in a stacked configuration, as shown. The individual laminates 28 are elongated substantially flat members fabricated from magnetostrictive material such as nickel or a nickel alloy which are coated with a layer of oxide. The oxide serves to insulate the adjacent laminates from each other.

Further, the individual laminates 28 are bonded together at each end 30,32 by a brazing process. However, in the present invention, the brazed ends 30,32 not only includes solder that covers all four sides of the device 26, but also include bars of solder 34,36 that extend transversely through the ends of the laminates 30,32, as shown.

According to the present invention, the individual laminates 28 each include openings which enable the bars of solder to be formed when the ends 30,32 are being brazed. In this particular embodiment, the openings are circular apertures. These apertures form cavities 38,40 when the laminates 28 are stacked and aligned before being bonded together. During the brazing process, solder flows into the cavities 38,40 to thereby form the solder bars 34,36 after the solder cools.

The addition of the solder bars 34,36 to the laminated structure of the magnetostrictive transducer 26 provides a number of advantages. One advantage is that the solder bars 34,36 serve to reinforce or increase the mechanical strength of the brazed ends 30,32. As a result of this reinforcement, the solder is prevented from cracking due to the vibration produced during operation of the magnetostrictive transducer 26.

As described earlier, during operation, conventional magnetostrictive transducers vibrate at an ultrasonic frequency which can cause cracking in the solder. However, in the present invention, such cracking is prevented since the solder bars 34,36 place more of the tension on the laminates 28 instead of the solder. This enables the individual laminates 28 to stay bonded together longer and thus provide a more durable and longer lasting device 26.

A further advantage of the magnetostrictive transducer 26 according to the present invention, is that the electrical contact between the laminates 28 is increased, which improves the eddy current conduction between the laminates 28. Since the ends of the laminates 30,32 are now joined by the exterior solder as well as by the solder bars 34,36, there is a greater surface area of interconnection between the laminates 28. This greater surface area enables an increase in the current conduction between the laminates 28 and thus improves the eddy current conduction.

Figure 4:
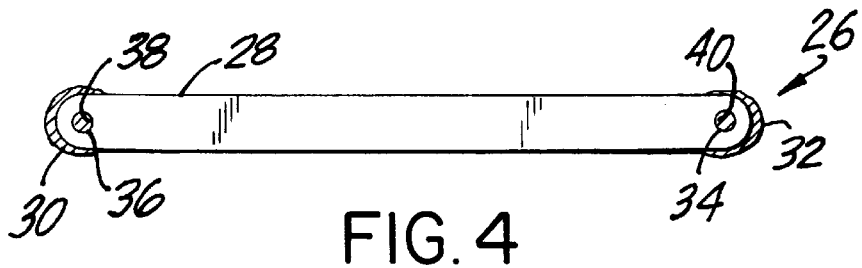
FIG. 4 is a view in section taken through section line 4—4 of FIG. 3.

A cross-sectional view of the magnetostrictive transducer 26 according to the present invention is shown in FIG. 4. This particular view more clearly shows the solder bars 34,36 being disposed within the apertures 38,40 of the individual laminates 28. This enables the solder bars 34,36 to extend transversely through the ends 30,32 of the stacked laminates 28. Such a configuration increases the mechanical strength of the abraded ends 30,32 and improves the eddy current conduction between the laminates 28, as previously described.

Figure 6:
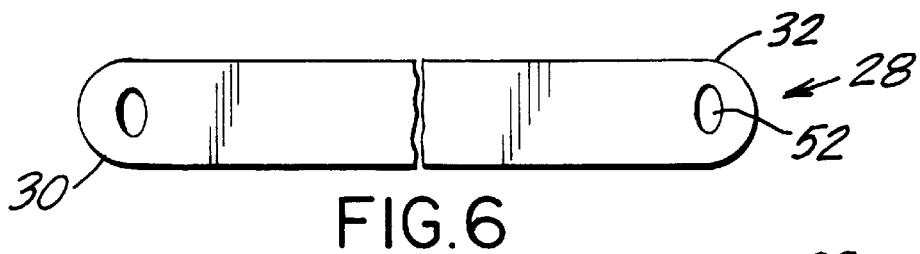
FIGS. 6–8 show embodiments of the individual laminates for the magnetostrictive transducer according to the present invention.
Figure 7:
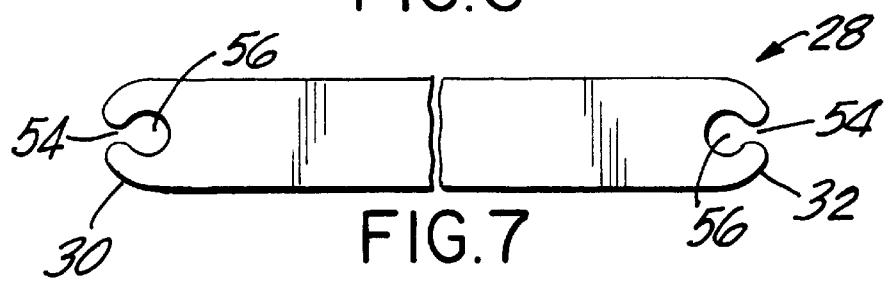
Figure 8:
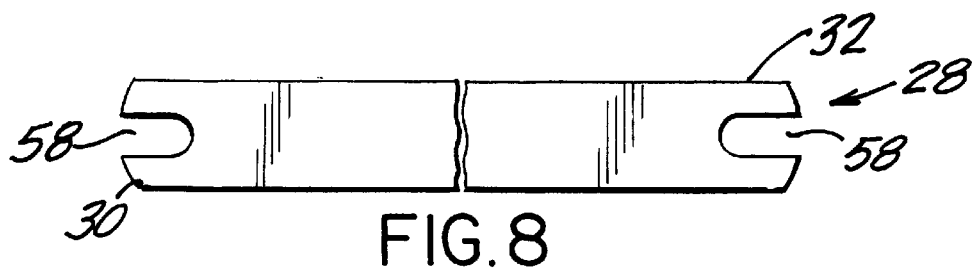
Figure 5A:
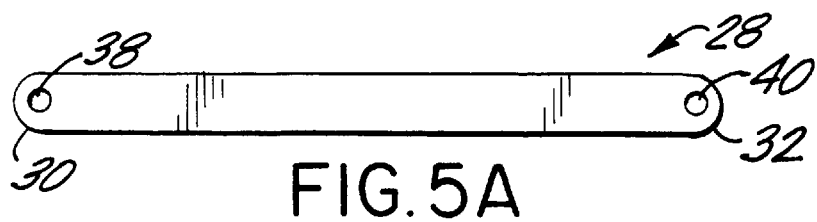
FIG. 5A–5D is a diagram illustrating the fabrication steps for the magnetostrictive transducer according to the present invention.

The steps involved in fabricating the magnetostrictive transducer according to the present invention is illustrated by FIGS. 5A–5D. In FIG. 5A, the individual laminates 26 must be first fabricated. The laminates 26 are preferably fabricated by first being cut from a long strip of magnetostrictive material such as nickel or a nickel alloy. After being cut, the apertures 38,40 are formed in the ends 30,32 of the laminates 26, by suitable means. Even though circular apertures are shown, other shapes are contemplated by the present invention as shown in FIGS. 6–8. Preferably, the apertures 38,40 have a diameter of 0.07 of an inch.

Figure 5B:
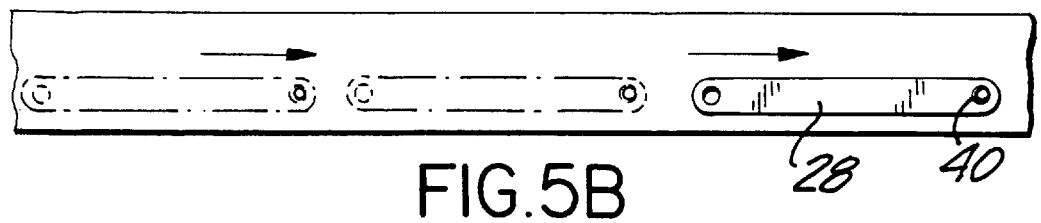

In FIG. 5B, the laminates 28 are then shown moved along an assembly line 42 for further processing. Such further processing includes coating the laminates 28 with a layer of oxide. Conventionally, the laminates 28 are moved along the assembly line by being pushed. However, this tends to deform the laminates 28 since bending can occur while the laminates are being pushed. According to the present invention, this bending can be prevented since one of the apertures 40 can be utilized to pull the laminates 28 along the assembly line 42 instead of being pushed.

Figure 5C:

In FIG. 5C, the laminates 28 are shown stacked on top of each other and aligned in order to be bonded together. As can be seen, the laminates 28 are aligned in this stacked configuration so that the apertures 38,40 form a continuous cavity that extends transversely through the stack of laminates as shown. Preferably the apertures 38,40 of the laminates 28 are axially aligned so that the solder bars later produced are straight and continuous. Conventionally, the laminations are stacked and aligned during a stamping assembly of the laminates. However, such a process can be enhanced by utilizing the apertures 38,40 for registration of the laminates during the stamping assembly.

Figure 5D:
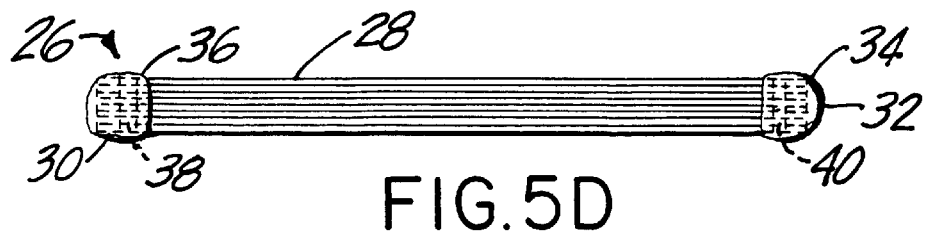

In FIG. 5D, the stack of laminates 28 is shown bonded together by a brazing process in order to form the magnetostrictive transducer according to the present invention. This brazing process includes removing the oxide layer from the ends of the laminates 30,32, heating up each end 30,32, and then applying flux and solder, preferably silver solder.

Conventionally, it takes a long time in order to entirely heat up the ends of the stack of laminates 28. This is due to the large number of laminates which are utilized. However, since the laminates 28 according to the present invention have openings, there is less material to heat up even though the same number of laminates is being utilized. Thus, in the present invention, the time required to heat up the ends of the stack 30,32 is significantly reduced. This is desirable since it enables the overall time for brazing the ends 30,32 to be much faster.

After heating up each end 30,32, the flux and solder is applied to the stack of laminates 28. As previously described, the solder flows on the outer surfaces of the laminates 28 as well as in the cavities formed by the apertures 38,40. This enables the solder bars 34,36 to be formed within the ends 30,32, as shown.

Other embodiments of the individual laminates 26 are shown in FIGS. 6–8. These other embodiments are intended to be utilized in the magnetostrictive transducer according to the present invention, as previously described for the embodiment including the circular aperatures. The embodiments shown in FIGS. 6–8 are the same as shown and described in conjunction with FIG. 5A except in the configuration of the ends 30, 32. FIG. 6 shows a laminate 28 that has oblong apertures 52 in the ends 30, 32. In FIGS. 7–8, instead of apertures being utilized, cutouts are utilized in the ends 30,32. FIG. 7 shows the cutouts each including a straight portion 54 that flairs outward into a circular portion 56. While FIG. 8 shows the ends 30, 32 each including a U-shaped cutout 58.

Figure 9:
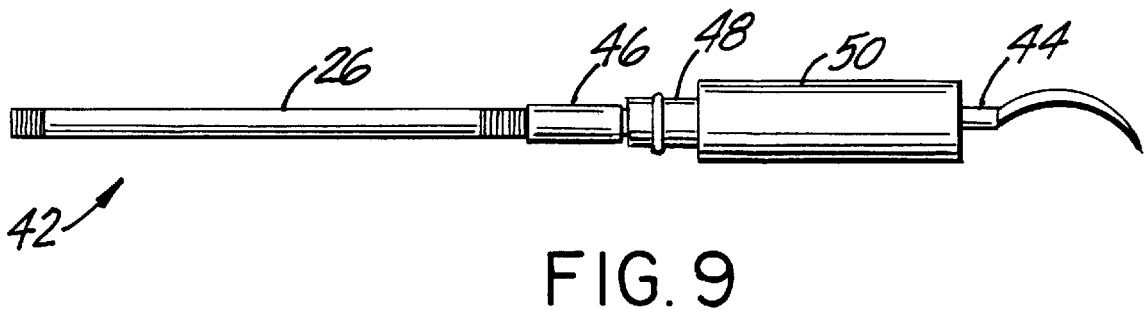
FIG. 9 is a perspective view one embodiment of an ultrasonic insert according to the present invention.

An example of embodiment of an ultrasonic insert made according to the present invention is shown in FIG. 9. The insert 42 includes a magnetostrictive transducer 26 according to the present invention, as previously described. Attached to one end of the magnetostrictive transducer 26 are other well known elements 46,48,50 that terminate in a tool element 44. The tool element in this embodiment is a dental scaler 44 utilized to scale teeth. Even though only a dental scaler is shown, other types of ultrasonic medical and dental devices are contemplated by the present invention.

There has been disclosed heretofore the best embodiment of the invention presently contemplated. However, it is to be understood that various changes and modifications may be made thereto without departing from the spirit of the invention.

What is claimed is:

1. A magnetostrictive transducer, comprising:

a plurality of magnetostrictive laminates each having a first end and a second end, wherein said first and second ends of said laminates both include an apertures formed therein;

said laminates arranged in a stacked configuration and bonded together by solder at said first and second ends, wherein said solder extends through said apertures of said laminates forming a solder bar therein, thereby bonding said laminates together with increased mechanical strength and also providing increased electrical contact between said laminates.

2. The transducer of claim 1, wherein said solder is disposed over outer surfaces of said first and second end of said stacked configuration of laminates.

3. The transducer of claim 1, wherein each of said laminates is an elongated substantially flat member coated with a layer of oxide.

4. The transducer of claim 3, wherein said elongated substantially flat member is fabricated from a material selected from the group consisting of nickel and nickel alloys.

5. The transducer of claim 1, wherein said apertures of said stacked configuration of laminates are axially aligned.

6. The transducer of claim 1, wherein said apertures in each end of said laminates is a circular aperture.

7. The transducer of claim 1, wherein said apertures in each end of said laminates is an oblong aperture.

8. An ultrasonic medical or dental insert, comprising:

a magnetostrictive transducer including a plurality of magnetostrictive laminates each having a first end and a second end, wherein said first and second ends of said laminates include apertures formed therein, said laminates arranged in a stacked configuration and bonded together by solder at said first and second ends, wherein said solder extends through said openings of said laminates forming a solder bar therein, thereby bonding said laminates together with increased mechanical strength and also providing increased electrical contact between said laminates; and a tool element mechanically connected to one end of said magnetostrictive transducer.

9. The insert of claim 8, wherein said solder is disposed over outer surfaces of said first and second end of said stacked configuration of laminates.

10. The insert of claim 8, wherein each of said laminates is an elongated substantially flat member coated with a layer of oxide.

11. The insert of claim 10, wherein said elongated substantially flat member is fabricated from a material selected from the group consisting of nickel and nickel alloys.

12. A method for producing a laminated type of magnetostrictive transducer, comprising the steps of:

forming a plurality of magnetostrictive laminates including an aperture at both a first end and a second end of said laminates;

coating said laminates with a layer of oxide;

arranging and aligning said laminates in a stacked configuration; and bonding said stacked configuration at said first and second ends of said laminates wherein solder extends through said apertures of said laminates forming a solder bar therein, thereby bonding said laminates together with increased mechanical strength and also providing increased electrical contact between said laminates.

13. The method of claim 12, wherein said laminates are formed by being cut from a long strip of material selected from a group consisting of nickel and nickel alloys.

14. The method of claim 12, wherein said bonding of said stacked configuration of said laminates is performed by a brazing process.

15. The method of claim 12, wherein said bonding further includes the solder being disposed over outer surfaces of said first and second ends of said stacked configuration of laminates.

16. The method of claim 12, wherein said aperture at said first and second ends has a configuration selected from the group consisting of a circular aperture and an oblong aperture.

* * * * *